(12) United States Patent
Eckerbom et al.

(10) Patent No.: US 9,861,298 B2
(45) Date of Patent: Jan. 9, 2018

(54) GAS SAMPLING LINE (75) Inventors: Anders Eckerbom, Vaxholm (SE); Robert Zyzanski, Stockholm (SE)

(73) Assignee: Masimo Corporation, Irvine, CA (US)

( * ) Notice: Subject to any disclaimer, the term of this patent is extended or adjusted under 35 U.S.C. 154(b) by 958 days.

(21) Appl. No.: 13/063,648

(22) PCT Filed: Sep. 11, 2009

(86) PCT No.: PCT/SE2009/051012
§ 371 (c)(1),
(2), (4) Date: Jun. 6, 2011

(87) PCT Pub. No.: WO2010/030226
PCT Pub. Date: Mar. 18, 2010

(65) Prior Publication Data
US 2011/0237969 A1    Sep. 29, 2011

(30) Foreign Application Priority Data

Sep. 15, 2008  (SE) ...................... 0801967

(51) Int. Cl.
*A61B 5/08* (2006.01)
*A61B 5/097* (2006.01)

(52) U.S. Cl.
CPC .............. *A61B 5/097* (2013.01); *A61B 5/082* (2013.01)

(58) Field of Classification Search
CPC ................................ A61B 5/082; A61B 5/097
(Continued)

(56) References Cited

U.S. PATENT DOCUMENTS 5,042,500 A * 8/1991 Norlien et al. ............... 600/532
5,703,161 A   12/1997 Steenblock et al.
(Continued)

FOREIGN PATENT DOCUMENTS

GB   2 175 208 A   11/1986
WO   98/46277 A2   10/1998
(Continued)

OTHER PUBLICATIONS

V.I. Bondar, B.D. Freeman, I. Pinnau "Gas Sorption and Characterization of Poly(ether-b-amide), Segmented Block Copolymers", 1999, Journal of Polymer Science: Part B: Polymer Physics, vol. 37, 2463-2475.*

(Continued)

*Primary Examiner* — Puya Agahi
(74) *Attorney, Agent, or Firm* — Knobbe, Martens, Olson & Bear, LLP (57) ABSTRACT

A gas sampling line having a channel for conducting respiratory gases from a patient respiratory interface to a gas monitor, the gas sampling line comprising, i.a., a gas sampling tube comprised of a polyether block amide material, the polyether segments of which comprise polyethyleneoxide. Use of a tube comprised of a polyether block amide material, the polyether segments of which comprise polyethyleneoxide, for sampling of respiratory gases; and a method for sampling of respiratory gases, the method comprising conducting respiratory gases through such a tube. A gas analysis system for analyzing respiratory gases, comprising a gas sampling line as defined above and a gas monitor connectable to the gas sampling line.

15 Claims, 1 Drawing Sheet

(58) Field of Classification Search
USPC .......................................... 600/529, 532, 543
See application file for complete search history.

(56) References Cited

U.S. PATENT DOCUMENTS

| | | | |
|---|---|---|---|
| 6,783,573 B2 | 8/2004 | Richardson | |
| 2003/0191405 A1* | 10/2003 | Rich et al. | 600/532 |
| 2004/0029467 A1* | 2/2004 | Lacroix | 442/76 |
| 2005/0161042 A1* | 7/2005 | Fudge et al. | 128/205.12 |
| 2006/0014059 A1 | 1/2006 | Wood | |
| 2010/0174239 A1* | 7/2010 | Yodfat et al. | 604/153 |

FOREIGN PATENT DOCUMENTS

| | | |
|---|---|---|
| WO | 2005/072297 A2 | 8/2005 |
| WO | 2006/120683 A2 | 11/2006 |

OTHER PUBLICATIONS

Pebax®, In Medical Applications, Arkema, Jun. 2007.*
Pebax®, Breathable Film, Arkema, Jun. 2007.*
Pebax®, Application Areas, Arkema, Jun. 2000.*
Pebax, in Medical Applications, Arkema, Jun. 2007.*
Pebax, Breathable Film, Arkema, Jun. 2007.*
Pebax, Application Areas, Arkema, Jun. 2000.*
Wikipedia.org: PEBA and PEG.*
Sridhar et al., Development of crosslinked polyether-block-amide membrane for CO2/CH4 separation, 2007, pp. 267-274.*
Supplementary European Search Report dated Nov. 30, 2012; Appln. No. EP 09 81 3309.
International Search Report: PCT/SE2009/051012; dated Dec. 21, 2009.
Flyer; "Our Materials Science Meets Your Medical Applications", Arkema 2009; 6 pages.
Pebax®, Product Range Overview, Arkema, Jun. 2007, 2 pages.
Pebax®, In Medical Applications, Arkema, Jun. 2007, 2 pages.
Pebax®, Breathable Film, Arkema, Jun. 2007, 2 pages.
Pebax®, Applications Areas, Arkema, Jun. 2000, 11 pages.
Yuri Yampolskii, et al; "Membrane Gas Separation", John Wiley & Sons, Ltd, 2010; pp. 257, 263.
V.I. Bondar, et al; "Gas Sorption and Characterization of Poly(ether-b-amide) Segmented Block Copolymers", Journal of Polymer Science: Part B: Polymer Physics, vol. 37, pp. 2463-2475, Apr. 26, 1999.
Eurpean Patent Office Third Party Observations, dated Sep. 28, 2012; Appln. No. 09813309.3-2319/2326246 PCT/SE2009051012.

* cited by examiner

GAS SAMPLING LINE

TECHNICAL FIELD

The present invention relates to a gas sampling line having a channel for conducting respiratory gases from a patient respiratory interface to a gas monitor, and to a gas analysis system comprising such a gas sampling line. Furthermore, the invention relates to the use of a tube for sampling of respiratory gases, and to a method for sampling of respiratory gases.

BACKGROUND ART

In respiratory care, it is often desirable to analyse and monitor the gas composition of a patient's exhaled and/or inhaled breathing gases. For instance, measurement of respiratory $CO_2$, $O_2$, $N_2O$ and anesthetic agents, such as halothane, isoflurane, enflurane, sevoflurane or desflurane, is useful in the care of critically ill patients undergoing anesthesia or mechanical ventilation. Typically, the gas concentrations of the patient's breathing gases are monitored by transferring a portion of the breathing gases through a sampling line to a suitable gas sensor or gas monitor.

The patient's exhaled breathing gases are usually saturated with moisture at body temperature. Thus, water naturally condenses when the gas sample is cooled to room temperature when passed through the sampling line. Collected condensate, together with secretion, bacteria or other contaminants possibly present in the breathing gases, may result in inaccurate readings at the sensor or even adversely affect a delicate gas monitor.

The accuracy of the gas concentrations obtained from a respiratory gas monitor also depends on the ability of the analyser system to direct the gas sample from the patient, through the tube of a sampling line to the gas sensor, without distorting the gas sample flow. One cause of distortion of the gas sample flow may be the adsorption on and/or absorption in the tube material of one or more of the components of the gas sample. Additionally, any physical obstacles in the gas sample line, such as valves or material seams, may distort the gas sample flow. Distortion of the gas sample flow, regardless of cause, can degrade rise time of the measured waveform making accurate analysis, especially at higher breath rates, difficult or impossible.

In order to protect a respiratory gas monitor from water and other contaminants, prior art gas sampling systems employs various means to separate liquids, bacteria etc. from the gas sample flow. It has for instance been known to include in the sampling line a water trap or another moisture separation means between the patient and the gas sensor. The challenge, however, is to design such a water trap or moisture separation means that achieves sufficient efficiency and capacity without distorting the gas sample flow.

U.S. Pat. No. 6,783,573 is directed to a gas sampling system for conducting respiratory gases. A gas sampling tube is configured to conduct the respiratory gases from a patient to a gas monitoring device. An output connector couples the gas sampling tube to the monitor. An output dryer tube is coupled between the gas sampling tube and the output connector. The output dryer tube is characterized by a tube length and a relative moisture removal efficiency. The relative moisture removal efficiency is dependent on the tube length. The tube length is selected to limit the moisture content of the respiratory gases being directed into the respiratory gas monitor to a predetermined level. The output dryer tube may be comprised of Nafion® or may be implemented using microporous filters or molecular sieves. An optional input dryer may be implemented using the same materials used to implement the output dryer.

WO 2005/072297 is directed to a liquid absorbing filter assembly and system using the same. It is disclosed a filter assembly for use in a sidestream gas sampling assembly. The filter assembly includes a hydrophilic liner lining the inner perimeter of a housing for wicking moisture from the gases to be monitored prior to the gases reaching a sensing mechanism. It is contemplated that the housing can be formed from an absorbent material or a gas drying material, such as Nafion®.

However, there is a need for improvement of prior art solutions for respiratory gas analysis in respect of, e.g., low distortion, long lasting moisture and/or water removal, or low cost.

SUMMARY OF THE INVENTION

An object of the present invention is to provide means for sampling of respiratory gases from a patient while protecting a gas monitor from moisture and/or water as well as providing a reading of high accuracy of gas components, including air gases, such as $CO_2$, $N_2O$ and anesthetic agents. Thus, it is an object of the invention to allow for a signal having a low distortion, particularly in a low flow gas sample and/or a gas sample from a patient having a high breath rate.

Another object of the present invention is to provide means for sampling of respiratory gases from a patient without employment of a conventional water trap. It is thus an object of the invention to provide a simple and cheap solution in comparison to conventional means comprising such water trap as well as to provide prolonged operating times in comparison to those of conventional means.

A further object of the present invention is to provide means of low material and production cost fulfilling the mentioned aspects of moisture and/or water removal as well as accurate gas component reading.

Another object of the present invention is to improve sidestream measurements of respiratory gases, i.e. when in order to influence a patient as little as possible a small fraction only of the inhaled and/or exhaled respiratory gas is diverted for measurement from the main flow of respiratory gas between a patient and, e.g. a breather apparatus.

Other objects or advantages of the invention should be apparent to a person skilled in the art after having read the description below.

In a first aspect of the invention, there is provided a gas sampling line having a channel for conducting respiratory gases from a patient respiratory interface to a gas monitor, the gas sampling line comprising a patient respiratory interface connector adapted to couple the gas sampling line to a patient respiratory interface;

a gas sampling tube adapted to conduct respiratory gases; and a gas monitor connector adapted to couple the gas sampling line to a gas monitor, wherein the gas sampling tube is comprised of a polyether block amide material, the polyether segments of which comprise polyethyleneoxide.

Thus, it has been surprisingly found that when passing a sample of respiratory gases through a gas sampling tube comprised of a polyether block amide material, the polyether segments of which comprise polyethyleneoxide, moisture and condensed water present in the gas sample permeate through the tube material to provide a dried gas sample, while components (such as $CO_2$ or anesthetic agents) of the gas sample passes the tube portion essentially undistorted (i.e. without being absorbed in or adsorbed to the tube material) to allow for an accurate reading at the gas monitor.

Polyether block amides (PEBAs) are thermoplastic elastomers well adapted for applications such as molded or extruded articles, films etc. They are block copolymers obtained by polycondensation of a carboxylic acid polyamide with an alcohol termination polyether. A polyether block amide elastomer consists of a regular linear chain of rigid polyamide segments and flexible polyether segments having the following general formula $$HO-[CO-A-CO-O-B-O]_n-H$$

where A represents the polyamide segment and B represent the polyether segment. Polyamide is a polymer comprising the characteristic amide group $$-NH-CO-$$

in the repeating units of the polymer chain. In the present invention, the polyether segments of the polyether block amide material comprise polyethyleneoxide, i.e. a polymer of the formula $$HO-[CH_2-CH_2-O]_n-H.$$

The polyamide segments of the polyether block amide material may comprise polyamide-12, polyamide-11 or polyamide-12.12, preferably polyamide-12. The nomenclature of the polyamides corresponds to an internationally recognised system, where a number indicates the number of carbon atoms in a compound used to prepare the polyamide. If only one number is given, it means that the polyamide is derived from a aminocarboxylic acid having that number of carbon atoms. If two numbers are given, the first number indicates the number of carbon atoms of a starting diamine and the last number indicates the number of carbon atoms of a starting dicarboxylic acid.

The polyether block amide material may comprise polyether segments and polyamide segments in a ratio of polyether to polyamide of from about 60:40 to about 40:60, preferably from about 60:40 to about 50:50.

A gas sampling line having a channel for conducting respiratory gases traversing, in addition to the patient interface connector and the gas monitor connector, only the above-mentioned gas sampling tube provides, in addition to its functional performance in view of moisture and water removal as well as non-adsorption and non-absorption of gas components, further advantages: Manufacture, e.g. extrusion, of the gas sampling tube from only one starting material is considerably simpler than a process of manufacture involving joining tube portions of different materials together. Furthermore, a smooth inner surface of the channel, without material seams, may more easily be achieved by such a gas sampling line. Thus, the risk for signal distortion is decreased.

It is, however, contemplated that parts of the channel for conducting respiratory gases may traverse tube sections of other materials, such as PVC or other conventional tube materials, included in the gas sampling line, in addition to the above-mentioned gas sampling tube. Such a design is preferred when a gas sampling line having a combination of different properties, as provided by different tube materials, is desired. It may also be a cost-effective solution to combine a lower priced tube material with the gas sampling tube, particularly for long gas sampling lines.

It is advantageous when the gas sampling line further comprises a drying assembly comprising
a casing; and
a hydrophilic member disposed within the casing and being in fluid contact with the channel,
wherein the casing is comprised of a second polyether block amide material, the polyether segments of which comprise polyethyleneoxide.

Fluid contact between the hydrophilic member and the channel may be obtained, e.g., by surrounding a portion of the channel by a part of the hydrophilic member or by disposing a part of the hydrophilic member within a portion of the channel. When the gas sampling line comprises such a drying assembly, water or moisture present in respiratory gases conducted in the channel may be absorbed in, adsorbed to and/or stopped by the hydrophilic member. The hydrophilic member provides a wicking action, transporting moisture or water to the casing through which it is removed, thus not accumulating in the drying assembly. As described above in connection with the gas sampling tube, moisture and condensed water permeate through the polyether block amide material of the casing. Consequently, the drying assembly, and thus the entire gas sampling line, may be used for a prolonged period of time without change thereof.

A drying assembly as disclosed above and further detailed below may also be applied in a conventional gas sampling line, i.e. a gas sampling line wherein the gas is conducted through a tube of a conventional tube material not permeable by moisture and/or water.

The hydrophilic member may consist of a hydrophilic filter material having a large filtering area and being able to absorb moisture and water, e.g. in the form of sudden bursts of condensed water not yet removed during passage of the sampled gas through the gas sampling line. The drying assembly is typically positioned, along the gas sampling line, close to the end intended for connection to a gas monitor, e.g. adjacent to the gas monitor connector, in order to provide a final hinder to any water or moisture not removed during passage of the sampled gas through the gas sampling line.

The polyamide segments of the second polyether block amide material may comprise polyamide-12, polyamide-11 or polyamide-12.12, preferably polyamide-12. The second polyether block amide material may comprise polyether segments and polyamide segments in a ratio of polyether to polyamide of from about 60:40 to about 40:60, preferably from about 60:40 to about 50:50. Further properties and advantages of second polyether block amide material resemble those of the first polyether block amide material and may be gathered above.

The drying assembly may extend along the outside of a member defining the channel. This is an advantageous arrangement in that the hydrophilic member may transport moisture or water to a large area casing, thus allowing for efficient moisture and water permeation through the casing material, while maintaining a compact design of the gas sampling line. In particular, it is to be mentioned that the drying assembly may extend along the outside of the gas sampling tube as well as along the outside of tube sections of other materials, included in the gas sampling line. Alternatively, it may be suitable to arrange the hydrophilic member within the gas sampling tube being comprised of the polyether block amide material. A portion of the gas sampling tube being comprised of the polyether block amide material may, in other words, surround the hydrophilic member, said portion of the gas sampling tube thus representing the casing of the drying assembly.

The drying assembly may further comprise a hydrophobic member disposed across the channel. The hydrophobic member acts as a hydrophobic filter allowing the sampled gases to pass while protecting the gas monitor from undesirable substances or objects (e.g. bacteria or other bodily excretions) present in the sampled gas and hindering any remaining water from reaching the gas monitor. The hydrophobic member may or may not be positioned within the housing.

Gas sampling lines according to the invention are typically single patient use disposables. The gas sampling lines may be adapted for a wide range of patient categories, such as infant, adult, or pediatric patients. It is particularly useful to provide a gas sampling line adapted for patients having a high breath rate, such as infants, and/or a weak respiration (i.e. providing a low gas flow in the gas sampling line), such as infants and/or pediatrics. The gas sampling lines may be adapted to a wide range of applications, such as gas sampling from intubated patients, or nasal and/or oral gas sampling. Accordingly, in order to serve different patient categories or to allow use in different applications, the patient respiratory interface connector may be a nasal prong, a nasal cannula, an oral prong, a conical fitting, or a male or female Luer end. Thus, it is to be understood that the term "patient respiratory interface" may refer to an organ, e.g. the nose, of a patient as well as to a connection point in the respiratory loop of a mechanically ventilated patient. Although the gas sampling lines may be provided in any length, a typical length suited for practical use would be 1 to 3 m.

Gas samples drawn through a gas sampling line according to the invention are typically intended for analysis in a gas monitor, such as a spectroscopic analyser. The gas monitor connector of the gas sampling line is preferably designed, together with the gas monitor receptacle, to provide a smooth gas path without a dead volume, to provide a safe no-break, no-leakage connection and a to allow for a practically convenient handling of the patient, the sampling line and the gas monitor. Typical features provided by a preferred combination of the gas monitor connector of the sampling line and a gas monitor receptacle are an audible or otherwise perceptible "click" feedback assuring an operator that the gas monitor connector has correctly "clicked" into place in the gas monitor receptacle, a rotatable connection of the gas sampling line to the gas monitor, facilitating an operator's handling of the gas analysis system, absence of any intermediate connection elements, such as adapters, between the gas monitor connector and the gas monitor receptacle, thus providing a smooth gas path while avoiding risks for undesirable leakage, detection, e.g. by optical sensors, of a correct connection of the gas sampling line to the gas monitor and allowing, e.g., a sampling pump or the analyser to operate only when a correct connection is established, thereby improving the lifetime of components of the gas analysis system, and/or visual signals informing an operator of the operational status of the gas analysis system, e.g. green light when in operation, red light if occluded and blue light if an anesthetic agent is detected.

In a second aspect of the invention, there is provided use of a tube comprised of a polyether block amide material, the polyether segments of which comprise polyethyleneoxide, for sampling of respiratory gases. Discussed above are advantageous compositions of the polyether block amide material.

In a third aspect of the invention, there is provided a method for sampling of respiratory gases, the method comprising conducting respiratory gases through a tube comprised of a polyether block amide material, the polyether segments of which comprise polyethyleneoxide. Again, advantageous compositions of the polyether block amide material are discussed above.

In a fourth aspect of the invention, there is provided a gas analysis system for analysing respiratory gases, comprising a gas sampling line as defined above and a gas monitor connectable to the gas sampling line. The gas analysis system may further comprise a respiratory device, such as a respirator, connectable to the patient respiratory interface.

DETAILED DESCRIPTION OF AN EMBODIMENT OF THE INVENTION

Figure 1:
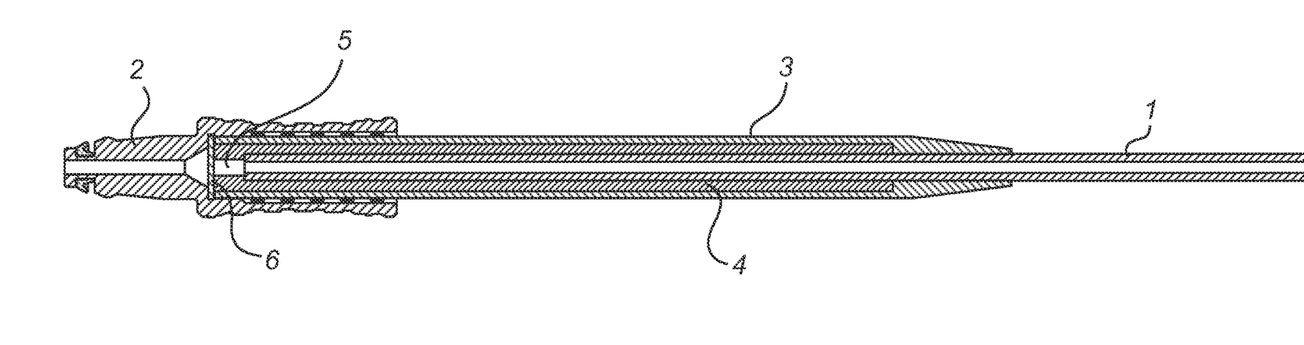
FIG. 1 is a schematic sectional view of a portion of a gas sampling line.

Referring to FIG. 1, some details of a an embodiment of a gas sampling line will be explained. The gas sampling line comprises a gas sampling tube 1, comprised of a material as specified above, connecting a patient respiratory interface connector (not shown) and a gas monitor connector 2. A gas monitor (not shown) may be coupled to the gas monitor connector 2. The gas sampling line further comprises a drying assembly comprising a housing 3, comprised of a material as specified above, and a hydrophilic member 4 disposed within the casing. The drying assembly 3, 4 extends along the outside of the gas sampling tube 1. The hydrophilic member is in fluid contact with a channel 5 for conducting respiratory gases traversing the gas sampling line. A hydrophobic member 6 is disposed across the channel 5.

When a sample of respiratory gases is conducted through the channel of the gas sampling line towards the gas monitor connector 2, moisture or water present in the sample will be adsorbed to or absorbed by the hydrophilic member 4. A wicking action of the hydrophilic member 4 will transport the moisture or water towards the housing 3. Subsequently, moisture or water will permeate the housing 3 and be removed into surrounding air. The respiratory gases will pass the hydrophobic member 6 on their way towards the gas monitor connector 2, whereas undesirable objects or substances (e.g. bacteria, body excretions) will be withheld by the hydrophobic member 6 and not reach the gas monitor. The hydrophobic member 6 also serves as an additional measure to stop water or moisture from reaching the gas monitor.

It is to be understood that the invention is not to be limited to the disclosed embodiment, but on the contrary, is intended to cover various modifications and equivalent arrangements included within the spirit and scope of the appended claims.

EXAMPLES

Characteristics and advantages of the present invention are further illustrated by the following, non-limiting, examples.

Preparation of Gas Sampling Tubes According to the Invention

Gas sampling tubes according to the invention were prepared by extrusion of a polyether block amide material (available from Atofina under the trade name Pebax®) to form a tubing having an inner diameter of 1 mm and an outer diameter of 2.5 mm, and subsequent cutting of the tubing to obtain gas sampling tubes having a length of 2 m. The composition of the polyether block amide material is shown in Table 1.

TABLE 1

Gas samping tube according to the present invention

| Tube no. | Composition |
|---|---|
| 1 | polyether block amide material of 55% polyethyleneoxide and 45% polyamide-12 |

Preparation of Comparative Gas Sampling Tubes

As comparative gas sampling tubes were used 2 m lengths of four different tubings having an inner diameter of 1 mm and an outer diameter of 2.5 mm. The composition of the tubing materials and the construction of the tubings are shown in Table 2. Comparative tubes 3-5 represent well-known embodiments of gas sampling tubes used in respiratory care for the conduction of gases to gas analysis equipment.

TABLE 2

Comparative gas sampling tubes

| Tube no. | Composition and construction |
|---|---|
| 2 | polyether block amide material of 53% polytetramethylene oxide and 47% polyamide-12 (extruded) |
| 3 | polyvinylchloride (extruded) |
| 4 | polyvinylchloride/polyethylene (co-extruded; inner layer PVC, outer layer PE) |
| 5 | polyvinylchloride + Nafion ® (1.9 m PVC joined to 0.1 m Nafion ®) |

Test Methods

All tests were performed at room temperature of about 22° C. at a gas flow of 50 ml/min through the gas sampling tube. In the tests, tube no. 5 was arranged so that in the direction of the gas flow, the Nafion® portion was upstream of the PVC portion.

A) Moisture test: A gas sample of moist air was passed from a simulated patient circuit, equipped with a heated humidifier, through a gas sampling tube to a water trap having a volume typical for disposable water traps for analysis of respiratory gases. The moist air leaving the simulated patient circuit had a relative moisture of 95-100% at 35-37° C. Water condensed in the tube was collected in the water trap and the time until the water trap had been filled with 200 µl liquid was recorded.

B) Water test: A gas sample comprising dry air and drops of water was passed from a simulated patient circuit, equipped with a syringe pump for delivery of water, through a gas sampling tube to a water trap having a volume typical for disposable water traps for analysis of respiratory gases. The syringe pump was set to deliver one droplet of water per minute, corresponding to 100 µl liquid per hour. The liquid was collected in the water trap and the time until the water trap had been filled with 200 µl liquid was recorded.

C) $CO_2$ accuracy: The sampling tube was connected between an equipment providing alternating two reference gases (5% $CO_2$ balanced $N_2$ and synthetic air) according to EN ISO 21647:2004 (Medical electrical equipment—Particular requirements for the basic safety and essential performance of respiratory gas monitors), FIG. 102, and a gas monitor. The measuring equipment was set to alternate the reference gases at a frequency corresponding to 40 breaths per minute. The ratio of $CO_2$ concentration measured by the gas monitor and $CO_2$ concentration of the reference gas was recorded.

D) Halothane accuracy: The sampling tube was connected between an equipment providing alternating two reference gases (5% $CO_2$, 5% halothane balanced $N_2$ and synthetic air) according to EN ISO 21647:2004, FIG. 102, and a gas monitor. The measuring equipment was set to alternate the reference gases at a frequency corresponding to 40 breaths per minute. The ratio of halothane concentration measured by the gas monitor and halothane concentration of the reference gas was recorded.

Results

The results are shown in Table 3. The gas sampling tube according to the invention (tube no. 1) provided an outstanding combination of desirable results in the moisture and water tests as well as in the $CO_2$ accuracy and halothane accuracy tests.

TABLE 3

| | Results | | | |
|---|---|---|---|---|
| Tube no. | A) Moisture test (h) | B) Water test (h) | C) $CO_2$ accuracy | D) Halothane accuracy |
| 1 | >24 | >24 | 0.98 | 0.98 |
| 2 | 2.5 | 2 | 0.98 | 0.98 |
| 3 | 2.5 | 2 | 0.98 | 0.73 |
| 4 | 2.5 | 2 | 0.98 | 0.98 |
| 5 | >24 | 2 | 0.97 | 0.74 |

The invention claimed is:

1. A gas sampling line having a channel for conducting respiratory gases from a patient respiratory interface to a gas monitor, the gas sampling line comprising
   a patient respiratory interface connector adapted to couple the gas sampling line to a patient respiratory interface;
   a gas sampling tube adapted to conduct respiratory gases; and
   a gas monitor connector adapted to couple the gas sampling line to a gas monitor,
   wherein the gas sampling tube is comprised of a first polyether block amide material, wherein the first polyether block amide material comprises polyether segments and polyamide segments in a ratio of polyether to polyamide from about 60:40 to about 40:60, and the polyether segments comprise polyethyleneoxide; and
   wherein a $CO_2$ component of the respiratory gases passes the gas sampling tube without being absorbed in or adsorbed to the tube material to allow for an accurate reading at the gas monitor.

2. The gas sampling line according to claim 1, wherein the polyamide segments of the first polyether block amide material is selected from the group consisting of polyamide-12, polyamide-11 and polyamide-12.12.

3. The gas sampling line according to claim 1, further comprising a drying assembly comprising
   a casing; and
   a hydrophilic member disposed within the casing and being in fluid contact with the channel, wherein the casing is comprised of a second polyether block amide material, the polyether segments of which comprise polyethyleneoxide.

4. The gas sampling line according to claim 3, wherein the polyamide segments of the second polyether block amide material are from the group consisting of polyamide-12, polyamide-11 and polyamide-12.12.

5. The gas sampling line according to claim 3, wherein the second polyether block amide material comprises polyether segments and polyamide segments in a ratio of polyether to polyamide from about 60:40 to about 40:60.

6. The gas sampling line according to claim 3, wherein the drying assembly extends along the outside of a member defining the channel.

7. The gas sampling line according to claim 3, wherein the drying assembly further comprises a hydrophobic member disposed across the channel.

8. A method for sampling of respiratory gases, the method comprising conducting respiratory gases through a tube comprised of a polyether block amide material, wherein the polyether block amide material comprises polyether segments and polyamide segments in a ratio of polyether to polyamide form about 60:40 to about 40:60, and the polyether segments comprise polyethyleneoxide; and wherein a $CO_2$ component of the respiratory gases passes the tube without being absorbed in or adsorbed to the tube material to allow for an accurate reading at the gas monitor.

9. The method according to claim 8, wherein the polyamide segments of the polyether block amide material are selected from the group consisting of polyamide-12, polyamide-11 and polyamide-12.12.

10. A gas analysis system for analysing respiratory gases, comprising a gas sampling line as defined in claim 1 and a gas monitor connectable to the gas sampling line.

11. The gas analysis system according to claim 10, further comprising a respiratory device connectable to the patient respiratory interface.

12. The gas sampling line according to claim 1, wherein the polyamide segments of the first polyether block amide material is polyamide-12.

13. The gas sampling line according to claim 1, wherein the first polyether block amide material comprises polyether segments and polyamide segments in a ratio of polyether to polyamide from about 60:40 to about 50:50.

14. The gas sampling line according to claim 3, wherein the polyamide segments of the second polyether block amide material are polyamide-12.

15. The gas sampling line according to claim 3, wherein the second polyether block amide material comprises polyether segments and polyamide segments in a ratio of polyether to polyamide from about 60:40 to about 50:50.

* * * * *

UNITED STATES PATENT AND TRADEMARK OFFICE
CERTIFICATE OF CORRECTION

PATENT NO. : 9,861,298 B2  
APPLICATION NO. : 13/063648  
DATED : January 9, 2018  
INVENTOR(S) : Anders Eckerbom Page 1 of 1

It is certified that error appears in the above-identified patent and that said Letters Patent is hereby corrected as shown below:

On the Title Page

In Column 1 (item (30)) at Line 31, Under Foreign Application Priority Data, change "0801967" to --0801967-1--.

In Column 2 (page 2, item (56)) at Line 22, Under Other Publications, change "Eurpean" to --European--.

In the Specification

In Column 6 at Line 23, Change "a an" to --an--.

In Column 6 at Line 39, Change "channel" to --channel 5--.

In Column 7 at Line 9 (approx.), Change "samping" to --sampling--.

Signed and Sealed this  
Tenth Day of July, 2018

Andrei Iancu  
*Director of the United States Patent and Trademark Office*

(12) INTER PARTES REVIEW CERTIFICATE (2411th)
United States Patent
Eckerbom et al.

(10) Number: US 9,861,298 K1
(45) Certificate Issued: Oct. 6, 2021

(54) GAS SAMPLING LINE (75) Inventors: Anders Eckerbom; Robert Zyzanski (73) Assignee: JPMORGAN CHASE BANK, NATIONAL ASSOCIATION

Trial Number:

IPR2019-01583 filed Sep. 6, 2019

Inter Partes Review Certificate for:

Patent No.: 9,861,298
Issued: Jan. 9, 2018
Appl. No.: 13/063,648
Filed: Jun. 6, 2011

The results of IPR2019-01583 are reflected in this inter partes review certificate under 35 U.S.C. 318(b).

INTER PARTES REVIEW CERTIFICATE
U.S. Patent 9,861,298 K1
Trial No. IPR2019-01583
Certificate Issued Oct. 6, 2021

AS A RESULT OF THE INTER PARTES REVIEW PROCEEDING, IT HAS BEEN DETERMINED THAT:

Claims 1-2 and 8-13 are found patentable.

* * * * *